United States Patent
Davis

(10) Patent No.: US 9,179,933 B2
(45) Date of Patent: Nov. 10, 2015

(54) GEAR DRIVEN TRIANGULATION

(75) Inventor: Emily Davis, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 751 days.

(21) Appl. No.: 13/412,093

(22) Filed: Mar. 5, 2012

(65) Prior Publication Data

US 2012/0253132 A1  Oct. 4, 2012

Related U.S. Application Data

(60) Provisional application No. 61/469,008, filed on Mar. 29, 2011.

(51) Int. Cl.
| | | |
|---|---|---|
| *A61B 1/32* | (2006.01) | |
| *A61B 17/34* | (2006.01) | |
| *A61B 17/42* | (2006.01) | |
| *A61B 19/00* | (2006.01) | |
| *A61B 17/00* | (2006.01) | |

(52) U.S. Cl.
CPC ............ *A61B 17/3423* (2013.01); *A61B 17/42* (2013.01); *A61B 19/201* (2013.01); *A61B 2017/00818* (2013.01); *A61B 2017/3447* (2013.01); *A61B 2017/3452* (2013.01)

(58) Field of Classification Search
CPC ........... A61B 17/0218; A61B 17/0281; A61B 17/12013; A61B 17/1285; A61B 17/29; A61B 2017/2902; A61B 17/2903; A61B 17/2906; A61B 17/2908
See application file for complete search history.

(56) References Cited

U.S. PATENT DOCUMENTS

| | | | |
|---|---|---|---|
| 4,898,577 A | 2/1990 | Badger et al. | |
| 4,997,419 A | 3/1991 | Lakatos et al. | |
| 5,176,128 A * | 1/1993 | Andrese | 600/204 |
| 5,441,483 A | 8/1995 | Avitall | |
| 5,487,377 A * | 1/1996 | Smith et al. | 600/204 |
| 5,498,231 A * | 3/1996 | Franicevic | 600/190 |
| 5,501,654 A * | 3/1996 | Failla et al. | 600/204 |
| 5,507,725 A | 4/1996 | Savage et al. | |
| 5,577,993 A * | 11/1996 | Zhu et al. | 600/204 |
| 5,603,689 A * | 2/1997 | Lucini | 600/201 |
| 5,626,595 A * | 5/1997 | Sklar et al. | 606/170 |
| 5,743,880 A | 4/1998 | Hlavka | |
| 7,250,027 B2 | 7/2007 | Barry | |
| 7,637,903 B2 | 12/2009 | Lentz et al. | |
| 7,682,319 B2 | 3/2010 | Martin et al. | |
| 7,708,182 B2 * | 5/2010 | Viola | 227/178.1 |
| 7,811,277 B2 | 10/2010 | Boulais | |
| 7,850,600 B1 * | 12/2010 | Piskun | 600/114 |
| 8,409,084 B2 * | 4/2013 | Battles | 600/204 |
| 8,685,003 B2 * | 4/2014 | Malkowski | 606/1 |
| 2002/0169362 A1 * | 11/2002 | Kan et al. | 600/170 |
| 2005/0014995 A1 | 1/2005 | Amundson et al. | |
| 2005/0165281 A1 * | 7/2005 | Ravikumar et al. | 600/204 |
| 2007/0049966 A1 | 3/2007 | Bonadio et al. | |

(Continued)

*Primary Examiner* — Mary Hoffman

(57) ABSTRACT

A surgical access port and method for achieving triangulation is disclosed, the surgical access port comprising a housing and an articulation structure. The housing is comprised of a cylindrical member having proximal and distal ends, and defining a longitudinal axis. The articulation structure is comprised of at least two lumens, each of the at least two tubular members disposed in a respective lumen, at least two rotating members disposed along each of the at least two tubular members, an actuating member, and a rigid member connecting each rotating member to each tubular member. The tubular members are configured to receive instruments for use in minimally invasive procedures.

14 Claims, 9 Drawing Sheets

(56) References Cited

U.S. PATENT DOCUMENTS

| | | |
|---|---|---|
| 2007/0078302 A1 | 4/2007 | Ortiz et al. |
| 2007/0208312 A1 | 9/2007 | Norton et al. |
| 2008/0009747 A1 | 1/2008 | Saadat et al. |
| 2008/0027279 A1* | 1/2008 | Abou El Kheir ............ 600/111 |
| 2008/0097391 A1 | 4/2008 | Feinberg et al. |
| 2008/0188869 A1 | 8/2008 | Weitzner et al. |
| 2008/0281293 A1 | 11/2008 | Peh et al. |
| 2009/0043299 A1 | 2/2009 | Racz |
| 2009/0157076 A1 | 6/2009 | Athas et al. |
| 2009/0188965 A1* | 7/2009 | Levin et al. ................ 227/179.1 |
| 2009/0192495 A1 | 7/2009 | Ostrovsky et al. |
| 2010/0121147 A1 | 5/2010 | Oskin et al. |
| 2010/0228092 A1* | 9/2010 | Ortiz et al. .................... 600/204 |
| 2010/0268035 A1* | 10/2010 | Oberlander et al. .......... 600/204 |
| 2011/0082339 A1* | 4/2011 | Elliott, III .................... 600/204 |
| 2011/0166422 A1* | 7/2011 | Ross et al. .................... 600/204 |
| 2012/0296169 A1* | 11/2012 | Kleyman et al. ............. 600/204 |
| 2013/0178713 A1* | 7/2013 | Kleyman et al. ............. 600/219 |
| 2013/0178837 A1* | 7/2013 | Malkowski ...................... 606/1 |
| 2014/0058205 A1* | 2/2014 | Frederick et al. ............ 600/202 |

* cited by examiner

GEAR DRIVEN TRIANGULATION

CROSS-REFERENCE TO RELATED APPLICATIONS

This application claims priority to, and the benefit of, U.S. Provisional Patent Application Ser. No. 61/469,008 filed Mar. 29, 2011, the entire contents of which are incorporated by reference herein.

BACKGROUND

1. Technical Field

The present disclosure relates generally to a surgical device for use in a minimally invasive surgical procedure. More particularly, the present disclosure relates to a surgical portal device adapted and configured to receive surgical instruments therein, and to reposition the distal ends of the surgical instruments that are placed through the surgical portal device.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gases and the deflation or collapse of the enlarged surgical site. In response to this, various access devices with sealing features are used during the course of minimally invasive procedures to provide an access for surgical objects to enter the patient's body. Each of these devices is configured for use through a single incision or a naturally occurring orifice (i.e. mouth, anus, or vagina) while allowing multiple instruments to be inserted through the device to access the working space beyond the device, generally an internal body cavity.

During procedures employing multiple surgical instruments through a single incision access device, it is advantageous to determine the position of the end effectors relative to each other and/or relative to a fixed reference point. This is desirable when one or more of the instruments includes an end effector that is articulable relative to the surgical instrument. Identifying the position of each end effector relative to the other end effectors and/or a common reference point is advantageous during a surgical procedure.

Some disadvantages of minimally invasive procedures include a lack of direct visualization of the surgical site and reduced dexterity of instruments, as compared to traditional open surgeries.

One surgical technique used to increase the ability of the surgeon to visualize and access critical anatomy is triangulation. Triangulation is a principle in which the positioning of the surgical instruments may be determined by having known initial positions of the instruments with respect to a given point, e.g., another device or instrument, and tracking the change in position from that initial position. One method of triangulation involves holding surgical instruments so that their tips form the apex of an imaginary triangle. By knowing the initial positions of surgical instruments with respect to a given point and by tracking the change in position, the coordinates of the surgical instruments are determinable.

One example, as disclosed by US Patent Application Pre-Grant Publication US2005/0234294, uses an articulating element disposed near a distal region and pivotally coupled to hinges by linkages.

Another example, as disclosed by US Patent Application Pre-Grant Publications US2007/0167680 and US2008/0051631, uses a rod connected to linking members which spread a set of arm members containing surgical devices apart when the rod is actuated.

Another example, as disclosed by US Patent Application Pre-Grant Publication US2008/0188868, uses a collar, a wedge, a balloon or bands to help maintain a divergence between the surgical devices.

Yet another example, as disclosed by U.S. Pat. Nos. 5,318,013; 5,395,367; and 5,511,564, uses an actuator including an articulated linking comprising a pair of arms pivotably connected to a push rod and to shafts of respective grasping forceps to enable relative spreading of the grasping forceps from a straightened or mutually parallel configuration to a spread use configuration.

In conventional minimally invasive surgical procedures, triangulation is achieved through insertion of multiple instruments through multiple openings. In most minimally invasive surgical procedures through a single incision, straight and rigid surgical instruments are inserted through a single incision. To control the instruments, a surgeon often crosses his hands. The lack of triangulation makes visualization and access of critical anatomy potentially difficult.

Furthermore, the placement of multiple instruments through a single incision increases the potential of interference among those instruments. It would be advantageous to space those instruments apart within the surgical site, without necessitating a larger incision.

Consequently, a continuing need exists for improved minimally invasive surgical devices.

SUMMARY

The present disclosure relates to surgical access ports for use in minimally invasive procedures where articulation of instruments disposed in a body cavity is required to reach off-axis points within the body cavity and determine the relative positioning of end effectors of surgical instruments disposed through the surgical access ports.

According to one embodiment of the present invention, a surgical access port is provided which includes a housing, at least two lumens extending through the housing, and an articulation structure disposed in the surgical access port. The housing is comprised of a cylindrical member having proximal and distal ends, and defining a longitudinal axis. Each lumen has an entrance aperture in the proximal end of the housing, and an exit aperture in the distal end of the housing. The body of the lumen gradually widens toward the distal end of the housing to accommodate the radial movement of surgical instruments under articulation control.

The articulation structure is envisioned to have different configurations. In one configuration, the actuation member may be a worm gear, with the rotating members abutting the actuation member as gear wheels. In this configuration, the actuation member is restricted from linear translation along the longitudinal axis.

In another configuration, the actuation structure is a toothed rack abutting rotating pinions. In this configuration, the actuation structure is free to translate along the longitudinal axis.

Connecting the rotating members to the tubular members are rigid arms. The rigid arms are connected to the rotating members such that they rotate about an axis substantially transverse to the longitudinal axis when the actuation structure is engaged, i.e., they move radially with respect to a longitudinal axis of the device. This rotation of the rigid arms thus effects angular displacement of the tubular members, and any surgical instruments disposed therethrough, from the longitudinal axis.

In some configurations, more than two tubular members, more than one actuation member, and/or more than two rotating members may be present, allowing for triangulation of multiple instruments with respect to multiple axes. In such configurations, actuation members may be oriented such that they articulate surgical instruments in multiple axes. Additionally, the spacing between tubular members may not be symmetrical about the longitudinal axis, so as to achieve a desired triangulation within a body member.

A handle may extend proximally from the actuation member, through the housing and further proximally so that the handle may be engaged by an operator. This handle provides direct control of the articulation structure to the operator of the surgical access port.

Also disclosed is a method for achieving triangulation, wherein the surgical access port is placed within a body member, surgical instruments are disposed in the surgical access port, and the actuating member is engaged such that articulation of the surgical instruments in a body cavity is achieved, allowing for triangulation of the instruments to determine the relative positioning of the end effectors of the surgical instruments.

Further disclosed herein are the steps of performing a minimally invasive procedure through the surgical access port, removing the surgical instruments from the surgical access port, and removing the surgical access port from the body member following surgery.

The various aspects of this disclosure will be more readily understood from the following detailed description when read in conjunction with the appended drawings.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
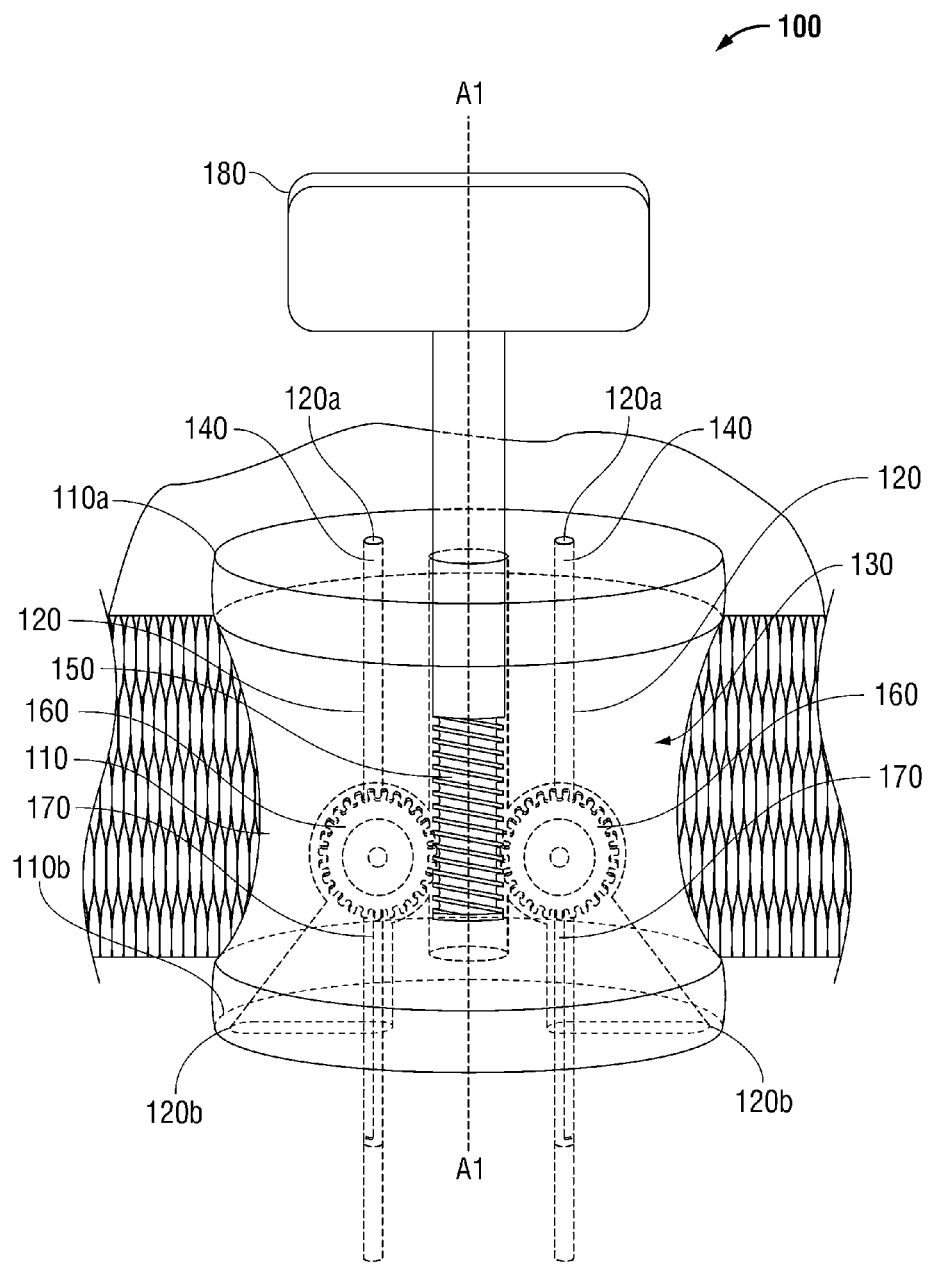
FIG. 1 is a side perspective view of a surgical access port according to an embodiment of the present disclosure, disposed in an incision site (shown in cut-away view) and containing an articulation structure (shown in phantom view)

Embodiments of the presently disclosed surgical access ports for use in minimally invasive surgery are described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user. The presently disclosed surgical access ports are usable in an incision through a patient's tissue or in a naturally occurring orifice (e.g. anus or vagina).

Referring initially to FIG. 1, a surgical access port, generally designated as 100, is shown. The surgical access port 100 is comprised of a cylindrical member 110 that has a generally hourglass profile. The cylindrical member 110 has a proximal end 110a and a distal end 110b and defines a longitudinal axis A1. Extending from the proximal end 110a to the distal end 110b of the cylindrical member 110 are two lumens 120. Each lumen 120 has an entrance 120a in the proximal end 110a of the cylindrical member 110, and an exit 120b in the distal end 110b of the cylindrical member 110. The lumens 120 widen toward the distal end 110b of the cylindrical member 110 to accommodate radial movement within the surgical access port 100 of objects under articulation control. The lumen exits 120b are similarly elongated for this purpose.

Disposed within the cylindrical member 110 is an articulation structure 130, which comprises two tubular members 140 disposed in the lumens 120, two worm wheels 160, and a worm gear 150. Extending proximally of the worm gear 150 and above the proximal end 110a of the cylindrical member 110 is a handle 180.

Figure 2:
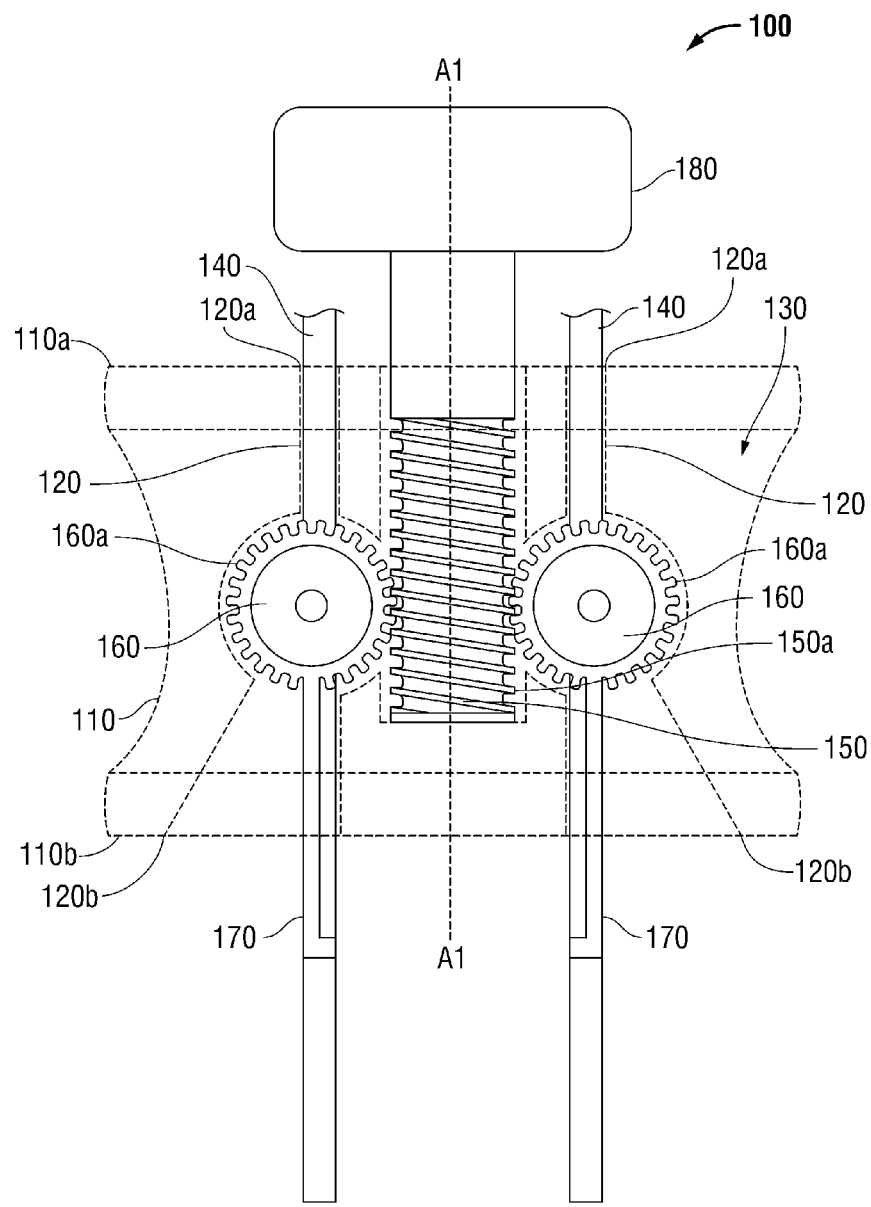
FIG. 2 is a side view of the surgical access port, with a cylindrical member (shown in phantom view), and the articulation structure comprising two lumens, two tubular members, two rigid arms, and two gear wheels abutting a worm gear.

Turning now to FIG. 2, a side view of the surgical access port 100 is shown, with the cylindrical member 110 in phantom view and the articulation structure 130 shown in standard view. Looking to the articulation structure 130, the worm gear 150 is configured to rotate about the longitudinal axis A1, but is restricted from axial translation along the longitudinal axis A1. The worm gear 150 abuts the worm wheels 160, and helical thread 150a is configured to engage the teeth 160a of the worm wheels 160. The worm wheels 160 are fixably attached to the rigid arms 170 by any suitable method, and may be integrally formed of the same member. The rigid arms 170, in turn, are attached to the tubular members 140. The attachment of the rigid arms 170 to the tubular members 140 is by way of an attachment to an outer surface of the tubular members 140, and may be achieved by any suitable coupling method, such as adhesion or clamping. Extending proximally from the articulation structure 130 is a handle 180. The handle 180 is operatively connected to the worm gear 150, and is configured such that an operator of the surgical access port 100 may engage the articulation structure 130 by engaging the handle 180. The handle 180 allows the operator of the surgical access port 100 to engage the articulation structure 130 from a point proximal of the cylindrical member 110.

Figure 3:
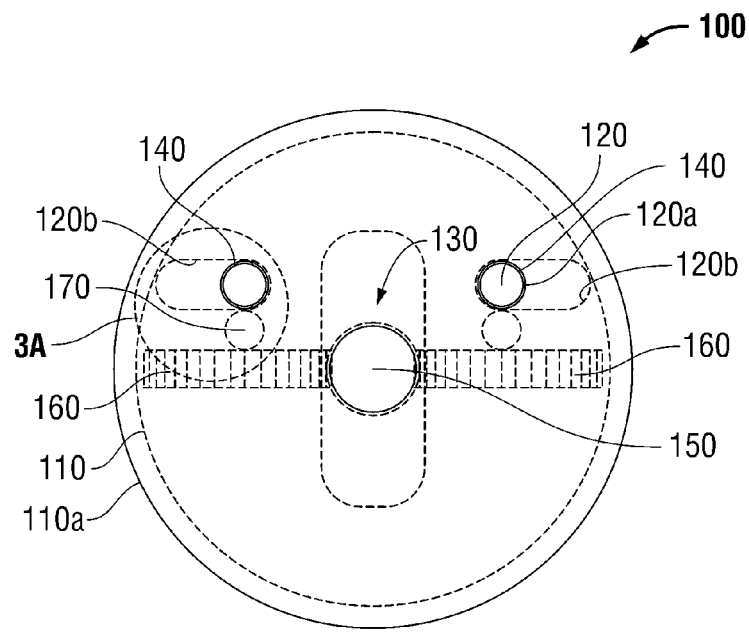
FIG. 3 is a top plan view of the surgical access port shown in FIG. 2, with the articulation structure shown in phantom view.

Referring to FIG. 3, a top plan view of the surgical access port 100 is shown. The lumens 120 containing the tubular members 140 extend from a proximal end 110a of the cylindrical member 110. At a distal end 110b (FIG. 1) of the cylindrical member 110, the exit aperture 120b of the lumens 120 can be seen in phantom view. The lumens 120 and exit aperture 120b of the lumens 120 widen towards the distal end 110b of the cylindrical member 110 such that the tubular members 140 and rigid arms 170 are allowed freedom of movement along an axis substantially transverse to the longitudinal axis A1 (FIG. 1). When the worm wheels 160 (shown in phantom) are set in motion by the worm gear 150, they cause the rigid arms 170 and tubular members 140 to rotate, and the tubular members move radially through the widened lumen 120 and lumen exit aperture 120b.

Figure 3A:
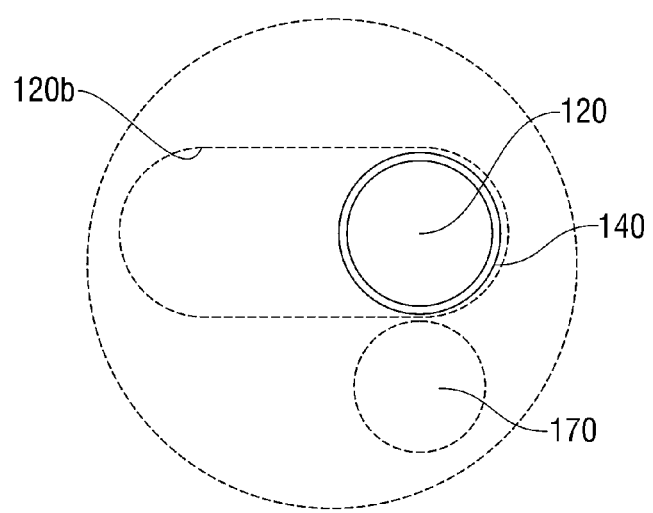
FIG. 3A is a partial detail view of the area surrounding a lumen, tubular member, and rigid arm in FIG. 3.

FIG. 3A shows an enlarged detail view of the area encompassing lumen 120, tubular member 140, and rigid arm 170 from the top plan view of FIG. 3. Tubular member 140 is shown disposed within the lumen 120. Shown in phantom view is the widened lumen exit 120b. Also shown in phantom view is the rigid arm 170 abutting the tubular member 140.

Figure 4:
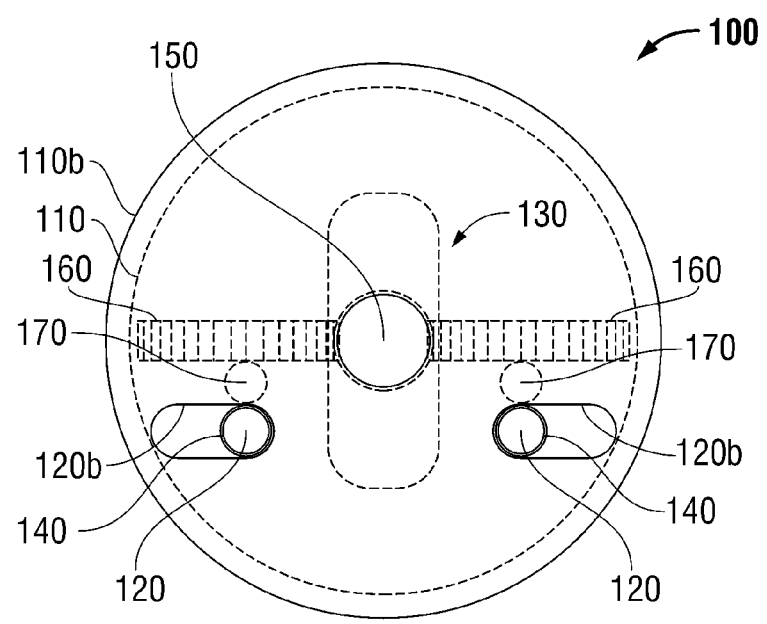
FIG. 4 is a bottom plan view of the surgical access port shown in FIG. 2, with the articulation structure shown in phantom view and showing shaped lumen exits at the distal end of the cylindrical member.

Turning now to FIG. 4, a bottom plan view of the surgical access port 100 is shown. In this view, the exit apertures 120b of the lumens 120 are shown in the foreground. As in FIG. 3, the rigid arms 170 are attached to the tubular members 140. Upon engagement of the articulation member 150 (FIG. 1), the tubular members 140 are displaced radially with respect to the longitudinal axis A1 (FIG. 1), and are allowed freedom of movement through the exit apertures 120b of the lumens 120. Thus, the end effectors 195b (FIG. 5) of the surgical instruments 195 (FIG. 5) are placed at off-axis positions within an internal body cavity 190b (FIG. 5).

Figure 5:
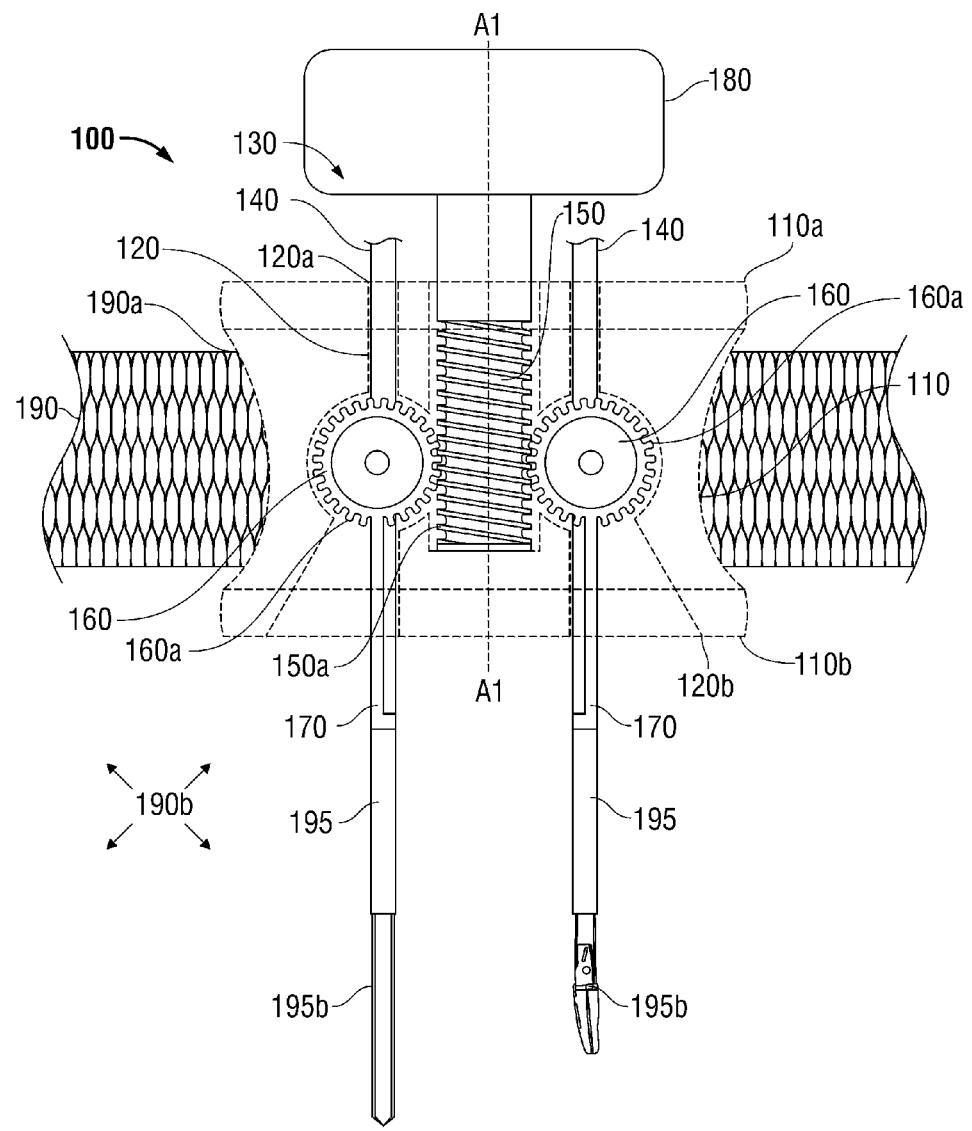
FIG. 5 is a side view of the surgical access port as shown in FIG. 2, disposed in a layer of tissue (shown in cut-away view) and with two surgical instruments inserted through the lumens.

As seen in FIG. 5, the surgical access port 100 is configured to be disposed in a layer of tissue 190, often at an incision site 190a. The proximal and distal ends 110a and 110b of the cylindrical member 110 may include rims or flanges to aid in anchoring the surgical access port 100 in the layer of tissue 190. Also shown is a pair of surgical instruments 195 having end effectors 195b, disposed in the tubular members 140. The surgical access port 100 is oriented such that the articulation structure 130 is substantially parallel to the longitudinal axis A1 and the surgical instruments 195 and end effectors 195b are disposed in the tubular members 140 and exit within the internal body cavity 190b.

In use, the operator of the surgical access port 100 engages the handle 180 and actuates the worm gear 150. Engagement of the handle 180 transmits torque to the worm gear 150, causing it to rotate about the longitudinal axis A1. The helical thread 150a of the worm gear 150 engages the teeth 160a of the worm wheels 160, and causes them to rotate about an axis substantially transverse to the longitudinal axis A1. The rotational motion of the worm wheels 160 in turn causes the rigid arms 170 to which they are attached to pivot about the axis of rotation of the worm wheels 160. As the rigid arms 170 are attached to the tubular members 140 and the surgical instruments 195 and end effectors 195b are inserted therethrough, the pivoting of the rigid arms 170 causes radial displacement of the surgical instruments 195 and end effectors 195b with respect to the longitudinal axis A1.

Figure 6:
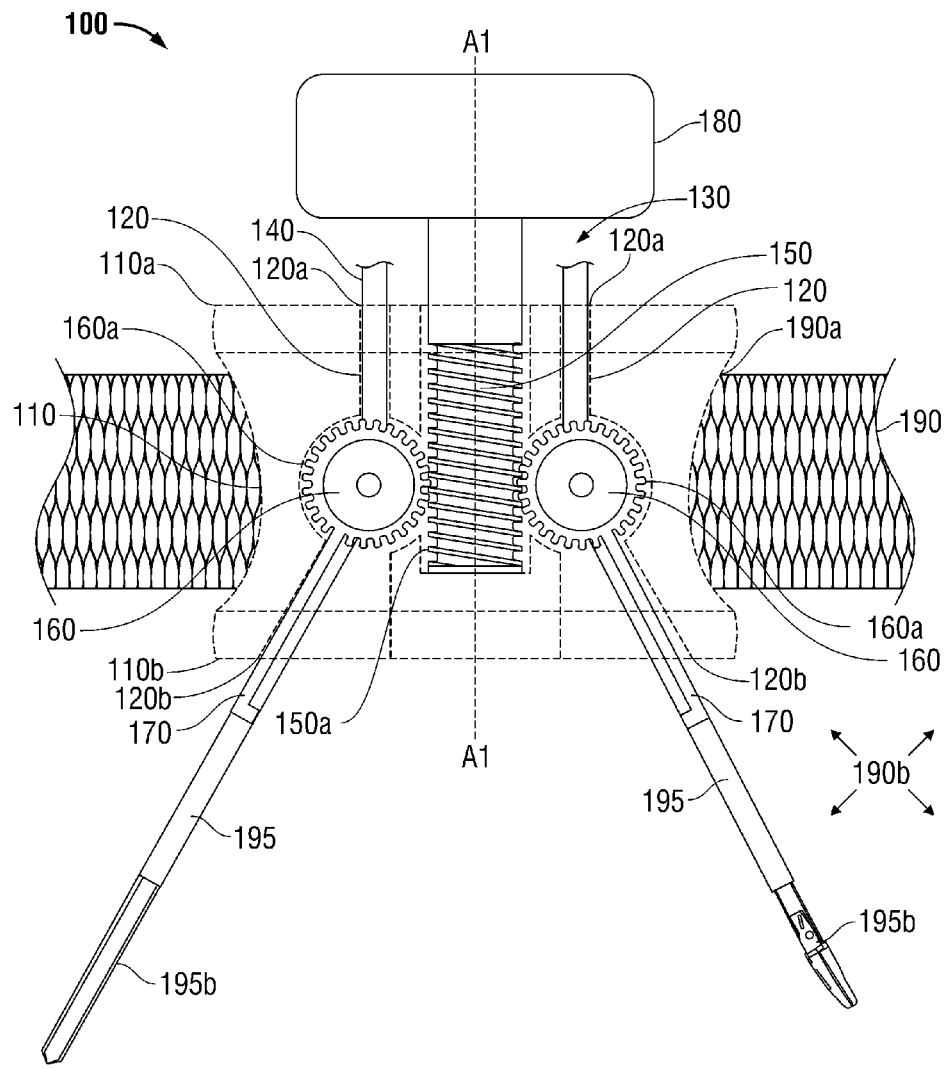
FIG. 6 is a side view of the surgical access port as shown in FIG. 5, with the articulation structure having been engaged and the tubular members and surgical instruments disposed at an angle with the longitudinal axis.

Turning now to FIG. 6, the surgical access port 100 is shown with the articulation structure 130 having been engaged. The worm wheels 160 have rotated in response to the rotation of the worm gear 150. The pivoting of rigid arms 170 thus cause tubular members 140 and the surgical instruments 195 disposed therethrough to deflect with respect to the longitudinal axis A1. This displacement is permitted by the gradually widened lumens 120 toward the distal end 110b of the cylindrical member 110 and the lumen exit apertures 120b. With worm gear 150 having been actuated a measured amount, and knowing the rate of rotation of the actuation structure 130, the operator of the surgical access port 100 can determine the relative spacing of the end effectors 195b of the surgical instruments 195 with respect to a known point, such as the cylindrical member 110 or the longitudinal axis A1.

Figure 7:
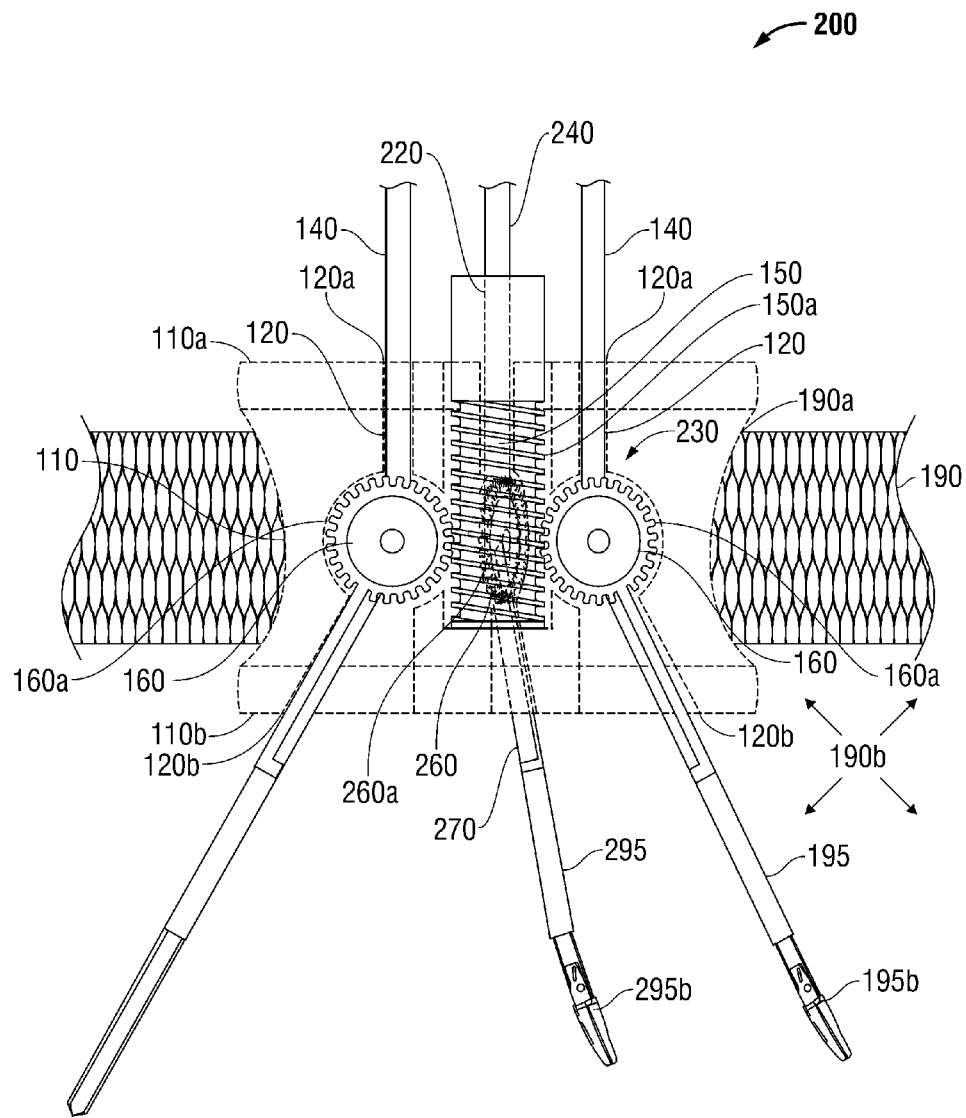
FIG. 7 is a side view of an embodiment of a surgical access port (shown in phantom view), wherein more than two lumens and corresponding gear wheels and surgical instruments are present in an articulation structure.

Referring now to FIG. 7, another embodiment of a surgical access port, designated 200, is shown. The articulation structure 230 of surgical access port 200 is configured to triangulate more than two surgical instruments 195, and includes at least a third surgical instrument 295 with end effector 295b. Disposed in the surgical access port 200 is a third lumen 220 containing a third tubular member 240, and a corresponding third worm wheel 260 and third rigid arm 270. The third worm wheel 260 is oriented on an axis substantially transverse to the longitudinal axis A1, but also different from the axis along which the first and second worm wheels 160 are disposed. The surgical access port 200 is configured such that upon actuation of the worm gear 150, the third worm wheel 260 will rotate about an axis substantially transverse to the longitudinal axis A1 (but different from the axes about which first and second worm wheels 160 rotate), and third tubular member 240 and third surgical instrument 295 will articulate in conjunction with the first two tubular members 140 and first two surgical instruments 195. As explained above, the operator of the surgical access port 200 can determine the relative spacing of the end effectors 195b, 295b of the surgical instruments 195, 295 with respect to a known point, such as the cylindrical member 110 or the longitudinal axis A1.

Figure 8:
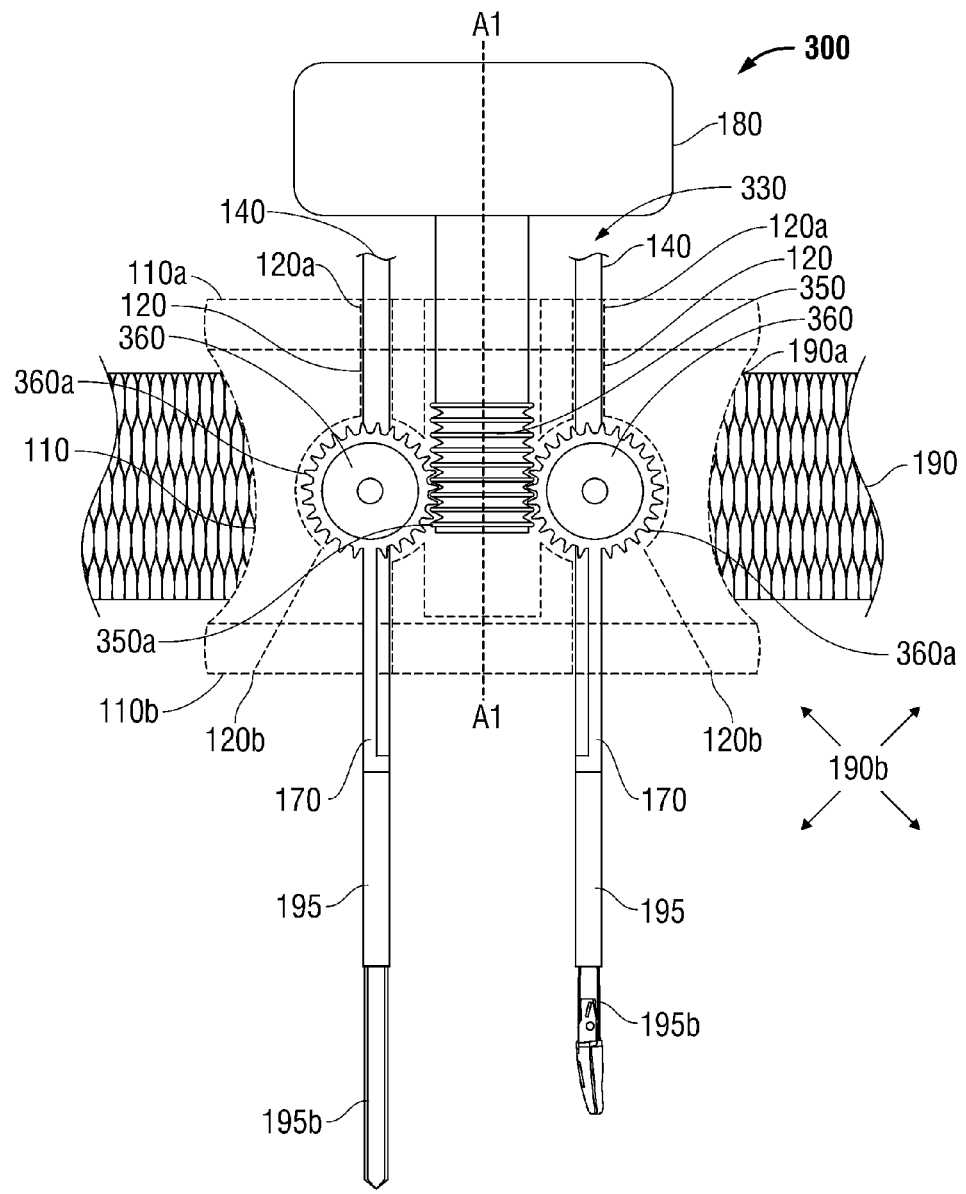
FIG. 8 is a side view of an embodiment of a surgical access port (shown in phantom view), wherein the articulation structure comprises a toothed rack abutting rotating pinions.

Turning now to FIG. 8, a surgical access port 300 is shown, which contains a toothed rack 350 as an actuation member. The toothed rack 350 is attached to a handle 180 extending proximally from the cylindrical member 110. In use, the handle 180 is engaged by an operator at the proximal end 110a of the cylindrical member 110, force is transmitted to the toothed rack 350. The toothed rack 350 translates along the longitudinal axis A1. As the toothed rack 350 moves distally along the longitudinal axis A1, the teeth 350a of the toothed rack engage the teeth 360a of pinions 360 and cause them to rotate about an axis substantially transverse to the longitudinal axis A1. The rigid arms 170, attached to the pinions 360, pivot about the axis about which the rotating members rotate, and cause the tubular members 140 to which they are connected to displace radially from the longitudinal axis A1.

Figure 9:
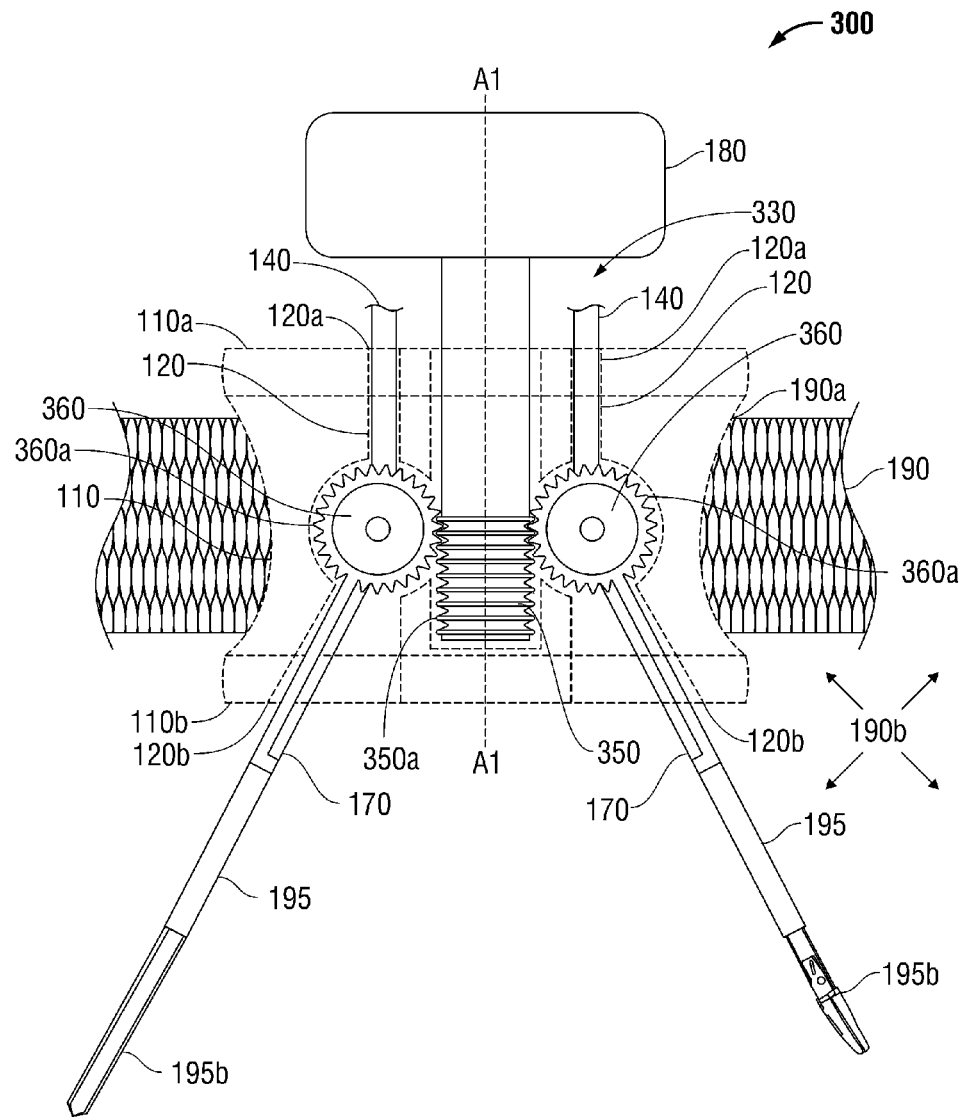
FIG. 9 is a side view of the surgical access port shown in FIG. 8, with the actuation structure having been engaged and the tubular members and surgical instruments disposed at an angle with the longitudinal axis.

Referring to FIG. 9, the surgical access port 300 is shown in an actuated state, with the toothed rack 350 displaced distally along the longitudinal axis A1. The pinions 360, rigid arms 170, and tubular members 140 have all pivoted about axes transverse to the longitudinal axis A1, resulting in the surgical instruments 195 disposed therethrough to be displaced radially to a desired position within the internal body cavity 190b. As in the previous embodiments, the known dimensions of the articulation structure 330 allows an operator of the surgical access port 300 to determine the relative spacing of the end effectors 195b of the surgical instruments 195 with respect to a known point, such as the cylindrical member 110 or the longitudinal axis A1.

It will be understood that various modifications may be made to the embodiments of the presently disclosed surgical access ports. Therefore, the above description should not be construed as limiting, but merely as exemplifications of embodiments. Those skilled in the art will envision other modifications within the scope and spirit of the present disclosure.

What is claimed is:

1. A surgical access port, comprising:
    a cylindrical member having a proximal end and a distal end and defining a longitudinal axis;
    at least two lumens extending through the cylindrical member from the proximal end to the distal end along the longitudinal axis;
    at least one articulation structure disposed in the surgical access port, the at least one articulation structure comprising:
        at least two tubular members, each tubular member disposed in a respective lumen;
        at least two rotating members, each rotating member disposed along one of the at least two tubular members;
        at least one actuating member in contact with the at least two rotating members; and
        two rigid members connecting the at least two rotating members to each of the at least two tubular members, wherein each rigid member is pivotable about an axis of rotation of at least one rotating member of the at least two rotating members connected therewith.

2. The surgical access port of claim 1, wherein the at least one actuating member is a worm gear.

3. The surgical access port of claim 2, wherein the at least one actuating member is inhibited from linear translation along the longitudinal axis.

4. The surgical access port of claim 2, wherein the at least two rotating members are gear wheels.

5. The surgical access port of claim 1, wherein the at least one actuating member is a toothed rack.

6. The surgical access port of claim 5, wherein the at least two rotating members are pinions.

7. The surgical access port of claim 1, wherein the at least one actuating member includes an engagement handle extending in a proximal direction.

8. The surgical access port of claim 1, wherein at least a third rotating member is oriented at an angle other than 180 degrees with respect to the at least two rotating members.

9. The surgical access port of claim 1, wherein each rotating member is rotatable about an axis transverse to the longitudinal axis of the cylindrical member.

10. A surgical access port, comprising:
    a cylindrical member having a proximal end and a distal end and defining a longitudinal axis;
    first and second lumens extending through the cylindrical member from the proximal end to the distal end along the longitudinal axis;
    an articulation structure disposed in the surgical access port, the articulation structure having:
        first and second tubular members, the first and second tubular members disposed in respective first and second lumens;
        first and second rotating members, one of the first and second rotating members disposed along one of the first and second tubular members;
        an actuating member in contact with the first and second rotating members, wherein the actuating member is a toothed rack; and
        first and second rigid members connecting the first and second rotating members to the first and second tubular members.

11. The surgical access port of claim 10, wherein the first and second rotating members are pinions.

12. The surgical access port of claim 10, further comprising a third rotating member oriented at an angle other than 180 degrees with respect to the first and second rotating members.

13. The surgical access port of claim 10, wherein the actuating member is inhibited from linear translation along the longitudinal axis.

14. The surgical access port of claim 10, wherein each of the first and second rotating members is rotatable about an axis transverse to the longitudinal axis of the cylindrical member.

* * * * *